(12) United States Patent
Taylor, Jr. et al.

(10) Patent No.: US 6,838,432 B2
(45) Date of Patent: Jan. 4, 2005

(54) TREATMENT OF SEPSIS WITH TAFI

(75) Inventors: Fletcher B. Taylor, Jr., Oklahoma City, OK (US); Laszlo Bajzar, Stoney Creek (CA)

(73) Assignees: Oklahoma Medical Research Foundation, Oklahoma City, OK (US); McMaster University, Hamilton (CA)

(*) Notice: Subject to any disclaimer, the term of this patent is extended or adjusted under 35 U.S.C. 154(b) by 200 days.

(21) Appl. No.: 10/246,662

(22) Filed: Sep. 18, 2002

(65) Prior Publication Data

US 2003/0114359 A1 Jun. 19, 2003

Related U.S. Application Data

(60) Provisional application No. 60/323,219, filed on Sep. 19, 2001.

(51) Int. Cl.[7] .............................................. A61K 38/00
(52) U.S. Cl. .............................. 514/2; 514/18; 435/68.1
(58) Field of Search ......................... 514/2, 18, 7, 397; 435/68.1, 226; 424/94.64, 145.1

(56) References Cited

U.S. PATENT DOCUMENTS

| | | | |
|---|---|---|---|
| 4,775,624 A | | 10/1988 | Bang et al. |
| 4,992,373 A | | 2/1991 | Bang et al. |
| 5,993,815 A | * | 11/1999 | Bajzar et al. ............ 424/145.1 |
| 6,071,514 A | * | 6/2000 | Grinnell et al. .......... 424/94.64 |
| 6,159,468 A | | 12/2000 | Carlson et al. |
| 2002/0147229 A1 | * | 10/2002 | Allerton et al. ............. 514/397 |
| 2002/0177560 A1 | * | 11/2002 | Greenfield et al. ........... 514/18 |

OTHER PUBLICATIONS

Bajzar, "Thrombin activatable fibrinolysis inhibitor and an antifibrinolytic pathway," Arterioscler. Thromb. Vasc. Biol. 20(12): 2511–2518 (2000).
Boffa, et al., "Characterization of the gene encoding human TAFI (thrombin–activatable fibrinolysis inhibitor; plasma procarboxypeptidase B)," Biochemistry 38(20): 6547–6558 (1999).
Campbell, et al., "Inactivation of C3a and C5a octapeptides by carboxypeptides R and carboxypeptidase N," Microbiol. Immunol. 46(2): 131–134 (2002).
Collard, et al. "Complement activation after oxidative stress. Role of the lectin complement pathway," Am. J. Pathol. 156: 1549–1556 (2000).
Daugherty, et al., "Polymerase chain reaction facilitates the cloning, CDR–grafting, and rapid expression of a murine monoclonal antibody directed against the CD18 component of leukocyte integrins," Nucl. Acids Res. 19(9): 2471–2476 (1991).

Gross, et al., "CD11b/CD18 mediates the neutrophil chemotactic activity of fibrin degradation product D domain," Thromb. Haemost. 77(5): 894–900 (1997).
Henry, et al., "Identification of Polymorphisms in the promoter and the 3' region of the TAFI gene: evidence that plasma TAFI antigen levels are strongly genetically controlled," Blood 97(7): 2053–2058 (2001).
Laudes, et al., "Anti–C5a ameliorates coagulation/fibrinolytic protein changes in a rat model of sepsis," Am. J. Path. 160(5): 1867–1875 (2002).
Laedley, et al., "Contribution of in vivo models of thrombosis to the discovery and development of novel antithrombotic agents," J. Pharmacol. Toxicol. Methods 43(2): 101–116 (2000).
Leavell, et al., "The role of fibrin degradation products in neutrophil recruitment to the lung," Am. J. Respir. Cell. Mol. Biol. 14: 53–60 (1996).
Nesheim, et al., "Myocardinal infarction and the balance between fibrin deposition and removal," Ital. Heart 2(9): 641–645 (2001).
Pereira, et al., "Human procarboxypeptidase B: Three–dimensional structure antimplications for thrombin–activatable fibrinolysis inhibitor," J. Mol. Biol. 321(3): 537–547 (2002).
Riedmemann, et al., "Increased C5a receptor expression in sepsis," J. Clin. Invest. 110(1): 101–108 (2002).
Taylor, et al., "Protein C prevents the coagulopathic and lethal effects of *Escherichia coli* infusion in the baboon," J. Clin. Invest. 79: 918–925 (1987).
Watanabe, et al., "Activity and antigen levels of thrombin–activatable fibrinolysis inhibitor in plasma of patients with disseminated intravascular coagulation," Thromb. Res. 104: 1–6 (2001).
Baxter Healthcare, Inc, "Protein C,"www.protein.com/proteinc/generallags.

* cited by examiner

*Primary Examiner*—Jon P. Weber
*Assistant Examiner*—Maury Audet
(74) *Attorney, Agent, or Firm*—Holland & Knight LLP

(57) ABSTRACT

A method for inhibiting and for reversing the dysfunctional response of vascular endothelial cells to an inflammatory stimulus in a subject in need of such therapy has been developed in which an effective amount of a pharmaceutical composition comprising thrombin-activatable fibrinolysis inhibitor (TAFI) combined with a pharmaceutically acceptable carrier and optionally other treatments is administered to the subject.

16 Claims, 4 Drawing Sheets

Anti-TAFI mAb Facilitates the Fibrinolytic Response to Sublethal *E. coli*.

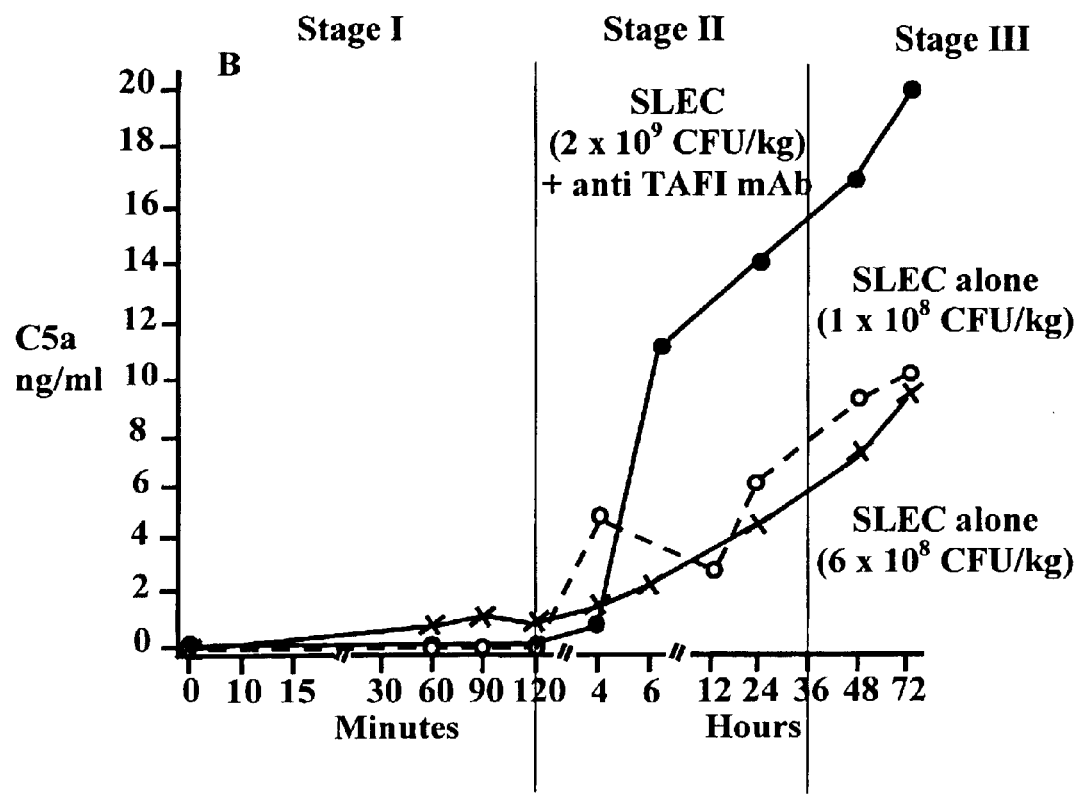
Figure 2: Antibody to TAFI Facilitates the C5a Response to Sublethal *E. Coli* (SLEC)

Anti-TAFI mAb Facilitates the Fibrinolytic Response to Sublethal *E. Coli*.

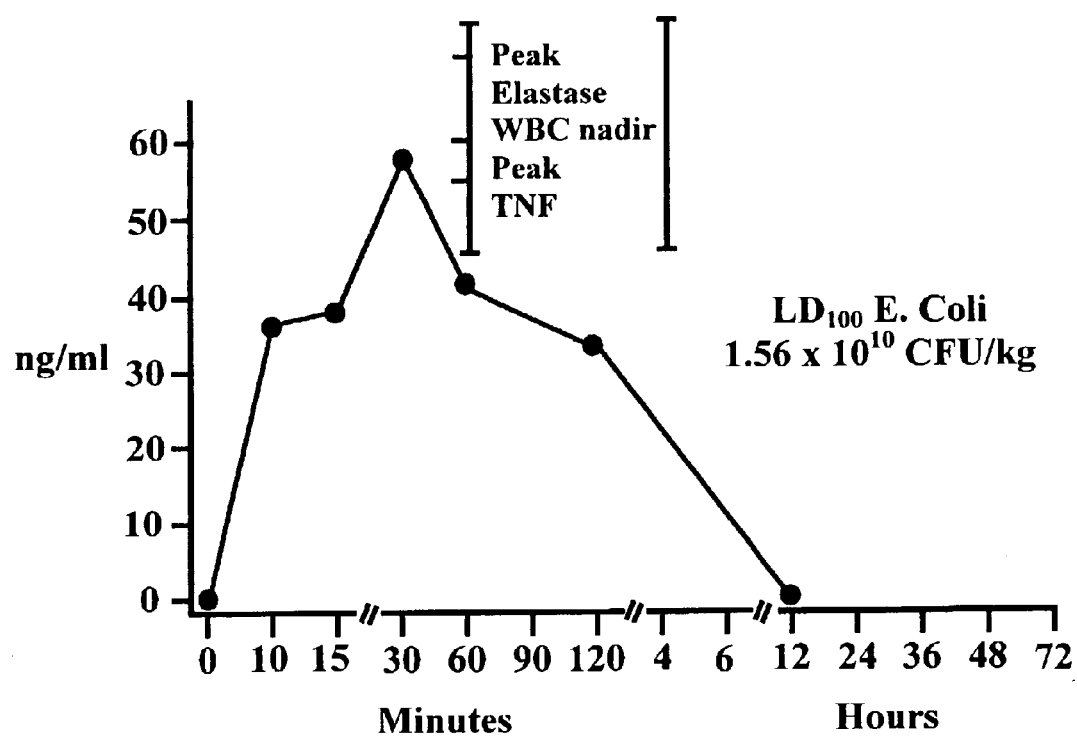

TREATMENT OF SEPSIS WITH TAFI

This application claims priority to U.S. Pat. No. 6,323,219 filed Sep. 19, 2001.

The United States government has rights in this invention by virtue National Institutes of Health grant No. RO1 GM37704-13.

BACKGROUND OF THE INVENTION

The present invention is in the general field of treatments of sepsis and other disorders characterized by endothelial cell dysfunction, specifically using thrombin-activable fibrinolysis inhibitor (TAFI) and analogues thereof administered in a therapeutically acceptable amount, alone or in combination with other active compounds such as activated protein C.

Vascular endothelium is comprised of the epithelial cells that form the lining of blood vessels. While vascular endothelium once was thought to be a passive barrier that simply channeled the blood, it now is known that endothelial cells are actively involved in the regulation of intravascular coagulation mechanisms and in the movement of fluid between the parenchyma and the intravascular space. The endothelium of the microvasculature further normally functions as a dynamic semi-permeable membrane. Intracellular mechanisms selectively control the porosity of the cell to various blood components. Normally, the membrane of endothelial cells is permeable to certain small physiologic molecules, such as water and nutrients, and to larger molecules under selected conditions, allowing them to pass as needed to and from the adjacent tissues. However, the endothelium normally is impermeable to larger molecules, such as plasma proteins that must remain in the blood to function. Although the endothelial mechanisms for regulating permeability and preventing thrombosis ordinarily are remarkably efficient, these mechanisms may be disrupted by an inflammatory stimulus which elicits the release of inflammatory mediators, and in particular the monokines tumor necrosis factor (TNF) and interleukin 1 (IL-1). In most cases, the release of these mediators is accompanied by activation of the plasma complement system.

An inflammatory stimulus that leads to release of inflammatory mediators occurs in a wide variety of pathological conditions. These conditions include sepsis, especially gram-negative septic shock, gram positive septic shock of the type caused by *Staphylococcus aureus*, and injuries involving substantial tissue damage, such as burns and crush injuries. Such a stimulus also may occur in adult respiratory distress syndrome and reperfusion inflammatory syndrome. The endothelial cell surface, as well as that of other cells in contact with the blood (e.g., fixed macrophages), is converted from an anticoagulant to a procoagulant state which permits intravascular coagulation. This, in turn, leads to consumption of coagulation factors, hence the term consumption coagulation. When this dysfunction is systemic, it is referred to as disseminated intravascular coagulopathy (DIC).

The mechanisms for regulating permeability are also affected so that the endothelial cell loses its ability to selectively control porosity. The endothelial cells swell and fluid begins leaking into the surrounding tissues, causing anoxia and parenchymal damage. This is accompanied by increased peripheral resistance, decreased venous return and in many instances, death due to shock. In most instances, for example septic shock, the response of the endothelium to the inflammatory stimuli involves both coagulopathy and abnormal permeability. However, in some conditions, both these dysfunctional responses may not occur. For example, some conditions may involve primarily uncontrolled permeability with minimal or no significant coagulopathy.

Sepsis is an infection-induced syndrome defined as the presence of two or more of the following features of systemic inflammation: fever or hypothermia, leukocytosis or leukopenia, tachycardia, and tachypnea or a supranormal minute ventilation. When an organ system begins to fail because of sepsis, the sepsis is considered severe. Each year, sepsis develops in more than 500,000 patients in the United States, and only 55 to 65 percent of those patients survive.

The major cause for sepsis is believed to be the excessive inflammatory response induced by endotoxin, or lipopolysaccharide (LPS), a component of Gram-negative bacteria. In plasma, LPS is released from the cell wall of growing bacteria, or bacteria damaged by complement or antibiotics. The LPS rapidly forms complexes with a variety of circulating proteins and lipids. Interaction of those free or bound LPS with the host monocytes and macrophages triggers the production of a cascade of proinflammatory cytokines, including tumor necrosis factor-alpha (TNF-alpha), interleukin 1 (IL-1) and interleukin 6 (IL-6). Systemic release of these cytokines with complement activation products and other materials induces excessive inflammatory response in both human and animals during bacteremia or overwhelming Gram-negative infection which may lead to septic shock and death.

More recently, investigations into the time course and extent of coagulation and fibrinolysis abnormalities in sepsis, their relationship to endothelial dysfunction, and the factors that may initiate these changes have highlighted the crucial role of an imbalance in hemostatic mechanisms. This imbalance can manifest as disseminated intravascular coagulopathy (DIC) and microvascular thrombosis, and may ultimately be one of the primary factors driving organ dysfunction and death. The pathophysiology of sepsis is currently viewed as one in which there is an uncontrolled cascade of inflammation, coagulation, and fibrinolysis. At each step in the cycle, auto-amplification processes contribute to the increased acceleration of coagulation abnormalities, inflammation, and endothelial injury.

Early events in the sepsis cascade triggered by the host's immune response have direct damaging actions on the vascular endothelium. Subendothelial structures are exposed and collagenases are liberated. Endothelial cells and monocyte/macrophages express tissue factor (TF), triggering the extrinsic coagulation cascade and accelerating the production of thrombin. Concurrently, the endothelial damage causes further exacerbation of inflammation, resulting in neutrophil activation, neutrophil-endothelial cell adhesion, ischemia reperfusion and further elaboration of inflammatory cytokines. These inflammatory processes further contribute to vascular endothelial dysfunction. Microvascular function is compromised, resulting in decreased tissue perfusion and hypoxemia with resultant organ dysfunction and failure.

Endogenous modulators of homeostasis, such as Protein C and AT-III, are consumed and their levels become deficient as the body attempts to return to a normal functional state. Under normal conditions, the endothelial surface proteins thrombomodulin and endothelial Protein C receptor (EPCR), activate Protein C and its modulating effects. In sepsis, the endothelial damage impairs this function of thrombomodulin and EPCR, thereby contributing to the loss of control. Left unopposed, the endothelial damage accumulates. This uncontrolled cascade of inflammation and coagulation fuels the progression of sepsis, resulting in hypoxia, widespread ischemia, organ dysfunction, and ultimately death for a large number of patients.

Inflammation is the body's normal response to infection. The body's initial response to an infection is to induce a pro-inflammatory state. Pro-inflammatory mediators, such as tumor necrosis factor (TNF-a), interleukin-1 (IL-1), interleukin-6 (IL-6), and platelet-activating factor (PAF) are released. These mediators have multiple overlapping effects designed to repair existing damage and limit new damage. To ensure that the effects of the pro-inflammatory mediators do not become destructive, the body again attempts to maintain its normal functional state by launching compensatory anti-inflammatory mediators, such as interleukin-4 (IL-4) and interleukin-10 (IL-10), which normally down-regulate the initial pro-inflammatory response.

In sepsis, regulation of the early response to infection is lost, and a massive systemic reaction occurs. These excessive or inappropriate inflammatory reactions are detrimental. An excess of the inflammatory mediators, such as TNF-alpha, IL-1, and complement activation products (e.g., C5a) are released, triggering an overwhelming physiologic response including neutrophil activation and adherence to the microvascular endothelium resulting in the development of diffuse capillary injury. Finally, excessive inflammatory reactions interfere with normal tissue function, leading to tissue damage and organ dysfunction.

In sepsis, the processes of inflammation and coagulation are intimately linked. Multiple inflammatory mediators that are released to fight infection also promote coagulation, which contributes to sepsis. In addition, the infectious agent itself can cause endothelial damage, which also promotes coagulation. Coagulation factors are activated when blood comes into contact with sub-endothelial connective tissues or with negatively charged surfaces that are exposed as a result of tissue damage. The first step is the binding of factor XII to a sub-endothelial surface exposed by an injury, thereby activating Factor XII. The activated factor XII activates factor XI. Eventually factor X is activated by a complex of molecules containing activated factor IX, factor VIII, calcium, and phospholipid. The end result of the clotting pathway is the production of thrombin, which converts soluble fibrinogen to fibrin. The insoluble fibrin aggregates and forms a clot, together with aggregated platelets (thrombi), blocking the damaged blood vessel and preventing further bleeding. In sepsis, multiple pro-inflammatory cytokines, such as IL-1alpha, IL-1beta, and TNF-alpha, induce the expression of TF on endothelial cells and monocytes, initiating coagulation. Tissue factor is a key mediator between the immune system and coagulation, and is the principal activator of coagulation. Tissue factor interacts with factor VIIa, forming the factor VIIa-TF complex, which activates factors X and IX. Amplification of coagulation via thrombin-mediated processes occurs with activated factors XI, VIII, and V. In the final stage, large amounts of thrombin are generated. Fibrin threads form a clump with activated platelets at the site of endothelial damage and a stable clot is formed.

Numerous investigational compounds have been studied for the treatment of sepsis. Many of these investigational therapies may have been unsuccessful because they modulate only a single pathophysiologic component of sepsis. Therapies targeting a wider range of mechanisms may be required to treat a disease process as complex as sepsis. Recently, the use of activated Protein C ("APC") to treat sepsis has been tested in phase III clinical trials by Eli Lilly. The APC was shown to be effective in reducing all cause mortality of 30% by 19%. However, approximately 24% of patients still die and it is desirable to have additional or alternative treatments for sepsis and other means of treating disorders characterized by endothelial cell dysfunction.

It is therefore an object of the present invention to provide a method and pharmaceutical compositions for treatment of sepsis and other disorders characterized by dysfunctional endothelium.

SUMMARY OF THE INVENTION

A method for inhibiting and for reversing the dysfunctional response of vascular endothelial cells to an inflammatory stimulus in a subject in need of such therapy has been developed in which an effective amount of a pharmaceutical composition comprising TAFI or an analogue thereof combined with a pharmaceutically acceptable carrier, and optionally other active ingredients such as activated protein C, is administered to the subject.

BRIEF DESCRIPTION OF THE DRAWINGS

FIG. 2 compares the responses of baboon C5a to sublethal $E.$ $coli$ plus anti-TAFI mAb with that of two baboons following sublethal $E.$ $coli$ alone.

FIG. 4 shows the C5a responses to the infusion of $LD_{100}$ $E.$ $coli$.

DETAILED DESCRIPTION OF THE INVENTION

Figure 1A:
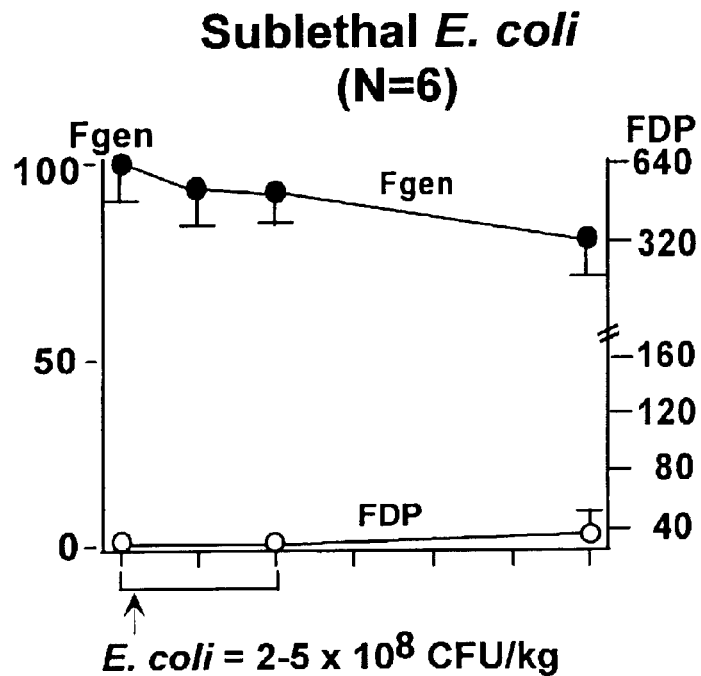
FIGS. 1A and 1B compare the fibrinolytic responses of baboons infused with sublethal $E.$ $coli$ alone (FIG. 1A) with that of a baboon infused with sublethal $E.$ $coli$ plus anti-TAFI mAb (FIG. 1B). Controls=2–5×$10^8$ CFU and experimental=5×$10^8$ CFU/kg $E.$ $coli$ plus anti-TAFI mAb (5 mg/kg).

A method of treating sepsis and other disorders characterized by impaired endothelial function has been developed in which an effective amount of TAFI is administered to the patient, prior to, or during sepsis, in an amount effective to promote fibrinolysis. The TAFI can be administered alone or in combination with other treatments, such as administration of activated protein C.
I. TAFI Formulations
TAFI Thrombin-activatible fibrinolysis inhibitor (TAFI; EC 3.4.17.20) is a 60-kDa plasma protein that has been shown to be identical to plasma carboxypeptidase B (CPB) and carboxypeptidase U (CPU). TAFI is a procarboxypeptidase and a member of the family of metallocarboxypeptidases. See Bajzar, Arterioscler. Thromb. Vasc. Biol. 20(12):2511–2518 (2000), for a recent review of the isolation and characterization of TAFI and its physiological activity. These enzymes circulate in plasma and are present in several tissues such as the pancreas. TAFI is activated by thrombomodulin (TM)-bound thrombin and specifically removes the C-terminal Lys and Arg of its substrates by its CPB activity. One of its target substrates is the C-terminal Lys residue in the alpha-chain of plasmin-digested fibrin, which is critical for plasminogen binding to fibrin. Thus, its removal seems to be the main mechanism through which TAFI inhibits fibrinolysis.

Both the cDNA and gene encoding human TAFI are known, as well as a number of polymorphisms in the protein encoding region as well as in the promoter. See, for example, Boffa, et al., Biochemistry 38(20):6547–6558 (1999) and Henry, et al., 97(7):2053–2058 (2001). As describes by Barbosa, et al., J. Mol. Biol. 321(3):537–547 (2002), TAFI circulates in human plasma as a zymogen bound to plasminogen. The structure of human pancreatic PCPB displays a 95-residue pro-segment consisting of a globular region with an open-sandwich antiparallel-alpha antiparallel-beta topology and a C-terminal alpha-helix, which connects to the enzyme moiety. The latter is a 309-amino acid residue catalytic domain with alpha/beta hydrolase topology and a preformed active site, which is shielded by the globular domain of the pro-segment. The fold of the proenzyme is similar to previously reported procarboxypeptidase structures, also in that the most variable region is the connecting segment that links both globular moieties. However, the empty active site of human procarboxypeptidase B has two alternate conformations in one of the zinc-binding residues, which account for subtle differences in some of the key residues for substrate binding. The reported crystal structure, refined with data to 1.6A resolution, permits in the absence of an experimental structure, accurate homology modelling of TAFI, which can be used to make TAFI mimetics.

For use as a pharmaceutical, the TAFI will preferably be a recombinant human TAFI. Either the zymogen or the activated form (TAFIa) of the enzyme can be administered. The zymogen can be activated prior to packaging and/or administration by addition of thrombin and thrombomodulin to the zymogen. In the preferred embodiment, the zymogen is administered early in disease, so that it is activated where needed.

Recombinant human TAFI can be produced using a variety of expression systems for recombinant protein expression. The protein can be expressed in either prokaryotic or eukaryotic expression systems. The recombinant protein can be harvested, and purified from cell lysates or from the culture medium. These expression systems are widely used and the protocols are known to those in the art. Prokaryotic expression systems such as *E. coli* or *Bacillus subtillis* are among the most popularly used. Bacterial systems offer advantages such as short expression times, ease of growth, and low cost.

Bacterial cells do not possess the cellular machinery to add posttranslational modifications such as phosphorylations or glycosylations. TAFI possesses glycosylation sites. Eukaryotic systems can be used to express the proteins. Yeast expression systems (*Saccharomyces cerevisiae*) can be used as cheaply as bacterial systems, with the same growth. Yeasts are becoming increasingly popular as host organisms for the heterologous expression of proteins by genetic engineering. The baculovirus/insect cell expression system is one of the most documented expression systems and is capable of generating large amounts of correctly folded and matured proteins. The most popular baculovirus used for gene expression is *Autographa californica* Multiple Nuclear Polyhedrosis Virus (AcMNPV). The baculovirus/insect cell expression system expresses recombinant proteins at extremely high levels in insect host cells and has a number of advantages over other expression systems including producing a high yield of recombinant protein, greater similarity to naturally occurring proteins, high recombinant efficiency, speed of expression, and scalable to volume production.

Expressing recombinant proteins in mammalian cells is the most expensive of these expression systems to use yet provides the closest approximation to the endogenous protein (i.e. proper folding and posttranslational modifications). Retroviral vectors are used to transfect cell lines to express the recombinant protein. The gene is inserted into a vector which is transfected into a packaging cell line. The replication-incompetent retroviruses containing the vector are collected and used to infect host cells. Stably integrated genes in mammalian cells are used for large scale production of proteins.

TAFI Regulation of Fibrinolytic Activity

TM down regulates fibrinolysis by stimulation of TAFI activation. However TM is also a cofactor in the activation of protein C. Activated protein C (APC) can up regulate fibrinolysis by limiting the activation of TAFI via the attenuation of thrombin production. TAFI activation is stimulated at low concentrations of TM but decreased at higher concentrations of TM. Similarly, the clot lysis times is increased at low concentrations of TM but decreased at higher concentrations of TM. The reduction of TAFI activation at high TM concentrations is dependent on a functional protein C pathway. The concentration of TM is therefore an important factor in the regulation of TAFI activation and in the regulation of fibrinolysis. High concentrations of TM result in up regulation of fibrinolysis, whereas low concentrations of TM have a down regulatory effect on fibrinolysis. These results suggest that fibrinolysis might be differentially regulated by TM in different parts of the body depending on the local TM concentration in the vasculature.

Coagulation and fibrinolysis are processes that form and dissolve fibrin, respectively. These processes are exquisitely regulated and protect the organism from excessive blood loss or excessive fibrin deposition. Regulation of these cascades is accomplished by a variety of mechanisms involving cellular responses, flow, and protein-protein interactions. With respect to regulation mediated by protein-protein interaction, the coagulation cascade appears to be more complex than the fibrinolytic cascade because it has more components. Yet each cascade is regulated by initiators, cofactors, feedback reactions, and inhibitors. Coagulation is also controlled by an anticoagulant pathway composed of (minimally) thrombin, thrombomodulin, and protein C. Protein C is converted by the thrombin/thrombomodulin complex to activated protein C (APC), which catalyzes the proteolytic inactivation of the essential cofactors required for thrombin formation, factors Va and VIIIa. An analogous antifibrinolytic pathway has been identified recently. This pathway provides an apparent symmetry between coagulation and fibrinolysis and is also composed of thrombin, thrombomodulin, and a zymogen that is activated to an enzyme. The enzyme proteolytically inactivates a cofactor to attenuate fibrinolysis.

TAFI Regulates Inflammatory Polypeptide Activity

However, unlike APC, which is a serine protease, the antifibrinolytic enzyme is a metalloprotease that exhibits carboxypeptidase B-like activity. Carboxypeptidase R (EC 3.4.17.20) (CPR) and carboxypeptidase N (EC 3.4.17.3) (CPN) cleave carboxy-terminal arginine or lysine residues from biologically active peptides such as kinins (bradykinen) or anaphylatoxins (C3a, C5a) in the circulation, thereby regulating their activities. Although CPN is present in a stable active form in plasma, CPR is generated from proCPR, a plasma zymogen, by proteolytic enzymes such as thrombin, thrombin-thrombomodulin complex and plasmin. Rat proCPR and CPN cDNA clones can induce enzymatic activities in culture supernatants of the transfected cells. mRNA of proCPR was detected only in rat liver by Northern hybridization and showed hepatocyte-specific expression. Expression of proCPR mRNA was enhanced following LPS injection, indicating that proCPR production is increased under inflammatory conditions.

Activation and Regulation of TAFI Activity

TAFI is activated by relatively high concentrations of thrombin in a reaction stimulated by thrombomodulin. In plasma an intact factor XI-dependent feed back loop via the intrinsic pathway is necessary to generate sufficient thrombin for TAFI activation. This thrombin generation takes place after clot formation with consequent down-regulation of fibrinolysis. A specific and sensitive assay for activated TAFI (TAFIa) was developed. Using this assay, the factor XI-dependent generation during clot formation was studied by Nesheim, et al. Ital. Heart 2(9):641–645 (2001). In the absence of thrombomodulin, addition of 20 nM thrombin to normal plasma generates 5–10% of the amount of TAFIa generated by 20 nM thrombin in the presence of 8 nM thrombomodulin. Minimal activation of TAFI is detected in factor II deficient plasma when clotting is initiated by 20 nM thrombin. Addition of 320–640 nM of thrombin to factor II deficient plasma results in the same amount of TAFIa as in normal plasma, suggesting that approximately 50% of factor II has to be converted to thrombin for extensive activation of TAFI.

A monoclonal antibody ("mAb") that neutralizes activated factor XII has no effect on TAFI activation, indicating that an intact contact system is not necessary for the activation of TAFI. The dependency of TAFI activation of factor XI was tested using a mAb that neutralizes activated factor XI. When plasmas from 13 healthy individuals were tested, this mAb reduced TAFI activation by 65% (range 35–89%). The results indicate that activation of TAFI in serum after clot formation can be quantitated and that it takes place in both factor XI-dependent and factor XI-independent mechanisms.

Thrombomodulin is a cofactor protein on vascular endothelial cells that inhibits the procoagulant functions of thrombin and enhances thrombin-catalyzed activation of anticoagulant protein C. Deletion of the N-terminal lectin-like domain and epidermal growth factor (EGF)-like domains 1 and 2 has no effect on TAFI or protein C activation, whereas deletions including EGF-like domain 3 selectively abolishes thrombomodulin cofactor activity for TAFI activation. Provided that thrombomodulin EGF-like domain 3 was present, TAFI competitively inhibits protein C activation catalyzed by the thrombin-thrombomodulin complex. A thrombomodulin construct lacking EGF-like domain 3 functions normally as a cofactor for protein C activation but is insensitive to inhibition by TAFI. Thus, the anticoagulant and antifibrinolytic cofactor activities of thrombomodulin have distinct structural requirements: protein C binding to the thrombin-thrombomodulin complex requires EGF-like domain 4, whereas TAFI binding also requires EGF-like domain 3.

Recently, it has been shown that Factor XI can be activated by thrombin, and that Factor XIa significantly contributes to the generation of thrombin via the intrinsic pathway after the clot has been formed. This additional thrombin, generated inside the clot, protects the clot from fibrinolysis. The lysis time is decreased twofold when TAFI is absent, when TAFI activation is inhibited by anti-TAFI antibodies, or when activated TAFI is inhibited by the competitive inhibitor (2-guanidinoethylmercapto)succinic acid. Inhibition of either TAFI activation or Factor XIa exhibits equivalent profibrinolytic effects. In the absence of TAFI, no additional effect of anti-Factor XI is observed on the rate of clot lysis.

TAFI Mimetics or Analogs

TAFI is useful as a target for compounds that turn on, or off, or otherwise regulate clotting or other disease processes mediated by TAFI. The assays described in the examples clearly provide routine methodology by which a compound can be tested. The in vitro studies of compounds that appear to act equivalently to TAFI are then confirmed by animal testing.

Drug Screening

A number of animal models are useful and predictive of efficacy in humans. For example, as reviewed by Leadley, et al. *J Pharmacol Toxicol Methods* March–April 2000; 43(2) :101–16, over the past two decades, great advances have been made in the pharmacological treatment and prevention of thrombotic disorders (e.g., tissue plasminogen activators, platelet GPIIb/IIIa antagonists, ADP antagonists such as clopidogrel, low-molecular weight heparins, and direct thrombin inhibitors). New research is leading to the next generation of antithrombotic compounds such as direct coagulation FVIIa inhibitors, tissue factor pathway inhibitors, gene therapy, and orally active direct thrombin inhibitors and coagulation Factor Xa (FXa) inhibitors. Animal models of thrombosis have played a crucial role in discovering and validating novel drug targets, selecting new agents for clinical evaluation, and providing dosing and safety information for clinical trials. In addition, these models have provided valuable information regarding the mechanisms of these new agents and the interactions between antithrombotic agents that work by different mechanisms. Genetic models have also been used in thrombosis/hemostasis research and pharmacology, for example, gene-therapy for hemophilia, is an example of how animal models have aided in the development of the therapies that are now being evaluated clinically.

Drug Design

Medicinal chemistry is an interdisciplinary approach used to design small molecules, such as organic chemicals or peptides, for use as therapeutic agents. Medicinal chemists use a variety of technology platforms to discover and design drugs. These include combinatorial chemistry, computational chemistry, molecular modeling, high-throughput screening (HTS), enzymology, and pharmacology. The goal is to identify portions of a molecule responsible for particular activities, such as receptor binding or protein interaction. These properties can then be exploited to rationally design more effective drugs. Based on the structure and properties of a lead drug candidate, combinatorial chemists synthesize a series of closely related analogs. Computational chemistry tools are then used to simulate the interactions of structural elements with macro-molecules, such as receptors, in order to correlate structure with activity. Scientists need to be able to predict function based upon structural elements. Computational chemistry tools include tools for 3-D structure analysis, quantitative structure-activity relationship analysis, and comparative molecular field analysis, among others. Several companies market software and services to help speed drug discovery and lead optimization programs. For example, Tripos Inc., St. Louis, produces a variety of "chemically intelligent" modeling and analysis tools through its discovery software program. Bio Balance, New York, is an example of a company that does computer modeling of proteins for drug design.

Molecular modeling applications use falls into two broad categories: interactive visualization and computational analyses. The latter involves objective, computational analysis and is based upon known biophysical features of the molecule and established mathematical concepts that describe those features. These two approaches to modeling can be used alone or collectively to computationally derive a structure. Furthermore, these tools also can be used to reconstruct best-fit models from known structures when researchers make theoretical substitutions, insertions, or deletions in the composition of the macromolecule. Three of the most prominent uses of modern molecular modeling applications are structure analysis, homology modeling, and docking. Structure analysis centers on computational visualization of a molecule, provided its 3-D atomic coordinates have been elucidated, usually by X-ray crystallography or nuclear magnetic resonance (NMR). This information usually resides in major, world-accessible databases including the Brookhaven Protein Data Bank for protein structures, the Nucleic Acids DataBase at Rutgers University for DNA structures, and the Cambridge Crystallographic Data Centre (CCDC) for small molecule (nonprotein/DNA/RNA) structures. Using structure analysis tools, investigators may dissect the intricate features of a molecule's structure or examine potential structural changes due to changes in the atomic or molecular composition of the molecule or macromolecule. Three-dimensional structural analyses give the researcher the ability to examine the spatial, electrostatic, hydrophilic/hydrophobic, potential bonding, or the relationships of the substitute residue with neighboring residues on the same or separate chains. Homology modeling has been very important these last few years, as researchers in academia and the pharmaceutical industry seek model structures for proteins whose crystal structures have not yet been solved. Homology modeling is also referred to as "comparative modeling" and "knowledge-based modeling." It is essentially the theoretical creation of a structure using structural elements borrowed from another protein within the same protein family (usually based on primary sequence and/or secondary structure features) whose crystal structure is known. The process involves alignment of the two sequences, usually performed by any of a number of bioinformatics tools. The result of this alignment is then fed into a homology modeling application, which uses the known crystal structure and the alignment to construct a "draft" (preliminary) structure for the "structureless" protein. This structure is then refined: loops are constructed (for "gapped" alignment regions), the residue side chain spatial placement is modified, and the entire "draft" homology structure is fine-tuned. A number of commercial and academic software packages perform homology modeling. Among the most widely used are INSIGHT II/HOMOLOGY and Modeler (MSI), Look/GeneMine (MAG), and SYBYL/COMPOSER (Tripos).

Docking modeling is used to better understand and model novel protein-protein and protein-ligand interactions (that is, receptor and ligand binding). This provides an avenue to examine and model receptor sites and assess potential ligands (drugs) and receptor-ligand associations. These techniques allow one to examine binding specificity and decipher the details of the atomic interactions involved in molecular recognition and catalysis. Some of the more widely used docking programs include AutoDock (Oxford Molecular Group), DOCK (Molecular Design Institute-UC San Francisco), FTDOCK (Biomolecular Modeling Laboratory), INSIGHT II (MSI), SYBYL/FLEXIDOCK (Tripos) and MidasPlus (Computer Graphics Laboratory, UC San Francisco). Important challenges in this area are optimizing the conformations of the ligand and receptor, and modeling the relevant non-bonded interactions between two species. The docking programs GOLD (CCDC) and Flex X (Tripos) take the approach of applying data from X-ray crystal structures in the Cambridge Structural Database which is a source of experimental information on non-bonded contacts. Many commercial applications such as Cerius$^2$, INSIGHT II (MSI), HyperChem (Hypercube), Look/GeneMine (MAG), SYBYL (Tripos)—provide transparent interfaces to these tools. Structural images created from X-ray and NMR coordinate files represent a snapshot in time for any given structure. In reality, the atoms and molecules are constantly moving as a result of thermal molecular motion and interactions with their environment. This interaction represents both passive and active processes (for example, interactions with nearby water molecules and substrate, respectively). In either case, these interactions translate into structural change for the macromolecule. The molecular dynamics approach to structure analysis seeks to understand and predict these structural changes based upon energy minimization. Dynamics analyses are based on an assessment (usually performed by molecular mechanics methods) of the free energy changes between two different structural states (a protein with and without bound ligand, for example). By mathematically extrapolating free energy changes, one can model a particular structure, which would have the appropriate calculated total free energy. These calculations can be reiterated for practically an infinite set of time points, thus allowing a researcher to model the temporal dynamics of macromolecule structure, for instance, as it performs some catalytic or binding function. Modeling programs that utilize molecular dynamics functions include HyperChem (Hypercube), INSIGHT II/Discover (MSI), AMBER, CAChe (OMG), SYBYL (Tripos), Alchemy 2000 (Tripos), Spartan (Wavefunction). Molecular mechanics emphasizes the potential energy of the molecule as a function of its component atoms, bonds and their angles, and charges—in general, the entire intramolecular environment. This approach attempts to calculate an energy potential for the entire molecule. Structure assignment is based on the assumption that the structure with the lowest energy potential represents a best fit for the molecule's structure as it exists in nature. Modeling programs that utilize molecular mechanical methods include HyperChem (Hypercube), SCULPT (ISI), SYBYL (Tripos), INSIGHT II (MSI), AMBER, CAChe (OMG).

Quantum mechanics methods of "structure" determination are based upon the electronic makeup of a molecule. Electron distribution is defined by one of many quantum theories; the most widely known and used is the molecular orbital theory. This and other theories provide the basis for mathematically determining a number of physicochemical parameters (electric multipole moments of a molecule, electron density distribution, electron affinities, nuclear atomic charge, electrostatic potentials, heats of formation, ionization energies, etc.) that may be utilized to construct a model structure. Quantum mechanisms offer advantages over the other methods in that it can be used to examine molecules at various electronic ("energy") states or during chemical bond formation and breakage. In essence, quantum mechanical methods are better at predicting chemical reality. Modeling with quantum mechanical methods is best for detailed analyses of molecule surface electrostatics, and thus protein-protein interactions and active/binding site interpretations (structure-function relationships, mechanistics of catalysis and/or binding). Modeling programs that utilize quantum mechanical methods include Cerius$^2$ INSIGHT II (MSI), HyperChem (Hypercube), and SYBYL (Tripos). Many modeling applications make use of several mathematical methods; for example, Mac/PC/UNIX SPARTAN (Wavefunction), SYBYL (Tripos), and INSIGHT II (MSI)

use a combination of molecular mechanics, quantum mechanical, and/or molecular dynamics methods. Multi-routine programs such as Cerius$^2$ (Tripos), INSIGHT II (MSI), Look/GeneMine (MAG), MidasPlus (Computer Graphics Lab), and SYBYL(Tripos) are especially important to researchers performing homology modeling and docking, where various kinds of computational routines are utilized in the model-building process. Such a process incorporates all physicochemical properties into the computational equation to derive the best thermodynamically stable structure, a structure that should depict a functional molecule.

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user. Although described above with reference to design and generation of compounds that could alter binding, one could also screen libraries of known compounds, including natural products or synthetic chemicals, and biologically active materials, including proteins, for compounds that are useful.

Antibodies

Antibodies are generated by standard techniques, using human or animal TAFI. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. These antibodies can then be used to create anti-Id antibodies which are equivalent to TAFI.

Because the methods for immunizing animals yield antibody which is not of human origin, the antibodies could elicit an adverse effect if administered to humans. Methods for "humanizing" antibodies, or generating less immunogenic fragments of non-human antibodies, are well known. The CDR grafting method described by Daugherty, et al., 1991 *Nucl. Acids Res.*, 19:2471–2476, incorporated herein by reference, can be used to humanize selected mouse monoclonal antibodies. The immunogenic stimulus presented by the monoclonal antibodies so produced may be further decreased by the use of AP Biotech's "Recombinant Phage Antibody System" (RPAS), which generates a single-chain Fv fragment (ScFv) which incorporates the complete antigen-binding domain of the antibody. Companies can also be contracted with to generate humanized antibodies. For example, Abginex, Freemont, Calif., generates antibodies with fully human protein sequences using genetically engineered strains of mice in which mouse antibody gene expression is suppressed and functionally replaced with human antibody gene expression, while leaving intact the rest of the mouse immune system.

Carriers

The TAFI can be formulated in standard pharmaceutical carriers for administration to patients in need thereof. These include saline, phosphate buffered saline, and other aqueous carriers. Controlled or sustained release formulation, wherein the protein is packaged in liposomes, polymeric microspheres or other controlled release delivery devices, are also well known in the art.

In the preferred embodiment, the TAFI, or TAFIa, is lyophilized and packaged in a vial in a discrete dosage, such as 5 mg. This is resuspended at the time of administration to the patient, typically by injection of sterile saline or water into the vial. The resuspended protein is then administered to the patient via catheter or infusion pump, set to deliver the desired dosage over a period of time. Drug can administered as a bolus (a single injection) or continuously, or in a combination thereof.

II. Other Active Compounds

In a preferred embodiment described below, the TAFI is administered with other active agents such as activated Protein C. Human protein C is a serine protease zymogen present in blood plasma and synthesized in the liver. For expression of complete biological activity, protein C requires a post-translational modification for which vitamin K is needed. The mature, two-chain, disulfide-linked, protein C zymogen arises from a single-chain precursor by limited proteolysis. This limited proteolysis is believed to include cleavage of a signal peptide of about 33 amino acid residues during secretion of the nascent polypeptide from the liver, removal of a pro peptide of about 9 amino acid residues (residues 34–42), and removal of amino acid residues 198 and 199 to form the two chains observed in the zymogen. The activation of the zymogen into the active serine protease involves the proteolytic cleavage of an ARG-LEU peptide bond (residues 211 and 212). This latter cleavage releases a dodecapeptide (residues 200–211) constituting the amino-terminus of the larger chain of the two-chain molecule. Protein C is a vitamin K-dependent serine protease produced in an inactive form by the liver. The zymogen circulates in the plasma and is activated by thrombin only at the surface of endothelial cells. The activation occurs when protein C binds to the thrombin complexed to thrombomodulin on the endothelial cell surface. When so activated, the protein C-protein S complex deactivates two of the cofactors of the coagulant pathway, factors Va and VIIIa, thereby inhibiting coagulation.

Protein C has been sequenced and is routinely produced recombinantly in bacterial or eucaryotic systems. See, for example, U.S. Pat. Nos. 4,775,624 and 4,992,373 Bang, et al. Protein C can also be isolated from plasma. Since it is somewhat species-specific, it is best to use APC of the same species of origin as the patient to be treated. The APC will typically be administered in a pharmaceutically acceptable carrier. In the preferred embodiment, the preparation will be administered intravenously and the carrier should be selected accordingly. Preferred carriers include normal saline, five percent dextrose in water, Lactated Ringer's Solution and other commercially prepared physiological buffer solutions for intravenous infusion. Of course, the selection of the carrier may depend on the subject's needs or condition.

Suitable formulations are described in U.S. Pat. No. 6,159,468. See also U.S. Pat. No. 6,071,514 for combination therapies with activated Protein C in combination with antiplatelet agents. Activated Protein C formulations are approved by the FDA for administration to patients with sepsis and marketed by Eli Lilly under the tradename XIGRIS™.

III. Methods of Prophylaxis and/or Treatment of Patients E. coli Sepsis and the Role of TAFI The typical clinical course of septic shock has been characterized as a four-stage process using the baboon septic shock model, J. Clin. Invest. 79:918–925 (1987).

Stage I begins with the inflammatory stimulus, e.g., a lethal infusion of *Escherichia coli*, and continues for about 120 minutes. In this stage, the scavenger cells (monocytes and macrophages) and PMN leukocytes are activated and the inflammatory mediators (TNF, IL-1, free hydroxyl radicals, C5a, bradykinen, elastase and others) are generated and released.

Stage II begins and continues for about four hours, or from two to six hours after the insult. During this stage, the mediators cause the endothelial cells to become inflamed or perturbed converting them from an anticoagulant to a procoagulant state. This includes induction of the expression of endothelial receptors (ELAM, ICAM) and activation and margination/adherence of neutrophils on to the microvascular endothelium not only by cytokines but also by complement activation products including C5a and C5a receptor. Fibrinogen levels fall and fibrin degradation products increase. The fibrinolytic activity of whole blood increases markedly by one to two hours and then decreases almost immediately at three hours after the insult. It is in Stages I and II that the regulatory anti-inflammatory, anticoagulant and profibrinolytic factors described earlier are overridden. These include IL-4, IL-10, protein C, antithrombin, and tissue plasminogen activator.

Stage III occurs at about six hours following the insult and continues for about four hours. In this stage, the endothelial cells lose thrombomodulin and EPCR function and undergo further loss of their ability to selectively control permeability resulting in further loss of fluid into tissues and in the deposition of fibrin. This stage and stage IV are characterized by a process of degradation of endothelial function rather than override. Liver damage is reflected by a rising SGPT level. The plasma level of activated protein C and the platelet count decrease during Stages I to III.

In the fourth and final stage, the parenchymal edema produces shunting, peripheral and eventually central anoxia, and decreased mean systemic arterial pressure. The platelet and protein C levels continue to fall. Death occurs typically about 24 to 32 hours after the insult.

The first two stages are directly induced by the *E. coli* organisms, which are cleared by 6–8 hours. These two stages are characterized by a "first round" of inflammatory/procoagulant/fibrinolytic activity (DIC) which is largely confined to the intravascular space. The third and fourth stages are induced by reperfusion of the micovasculature and oxidative stress following an initial vasospasm and ischemia. These latter two stages are characterized by a second round of inflammatory/procoagulant/fibrinolytic activity secondary to the oxidative stress and which involves the perivascular tissues as well as the intravascular contents.

Depending on the immune, endocrine, and metabolic states of the host at the time of challenge and depending on the intensity of the insult, these stages either may follow each other in a more or less orderly sequence leading to organ failure or they may be compressed into a single composite agonal inflammatory/coagulopathic collapse, or one or the other of these stages may dominate (e.g., a rapid catastrophic loss of intravascular volume and shock from capillary leak, (Stage I dominates), or a slowly developing irreversible microvascular thrombosis and renal failure with thrombocytopenia (Stage III dominates).

Both the protein C and TAFI networks operate through the endothelial thrombomodulin receptor to regulate this four-stage response. While protein C and TAFIa are described principally as anticoagulant and antifibrinolytic agents, they also exhibit antiinflammatory properties. These include, but are not limited to, down regulation of the production of TNF and chemotactically active fibrin degradation products (FDP) Gross, et al., Thromb. Haemost. 77(5):894–900 (1997); Leavell, et al. Am. J. Respir. Cell. Mol. Biol. 14:53–60 (1996); by activated protein C (APC) and the inactivation of vasoactive, chemotactically active polypeptides (e.g., C5a, bradykinen) by TAFIa.

Role of TAFI (Sublethal *E. coli* Model)

The role of endogenous TAFI in this model of *E. coli* sepsis is shown by comparing the fibrinolytic (FIG. 1) and inflammatory (Table 1, FIG. 2) responses of sublethal *E. coli* alone with those following sublethal *E. coli* plus anti TAFI antibody.

The baboons in FIG. 1 received a sublethal infusion of *E. coli* (either $2-5 \times 10^8$ CFU/kg, control, or $5 \times 10^8$ CFU/kg), infused over a 2-hour period. Treatment animals also received 5 mg mAb to TAFI/kg body weight 30 minutes before the initiation of the bacterial infusion. Samples were collected at 0, 1, 2, 4, 5 and 6 hours.

Figure 1B:
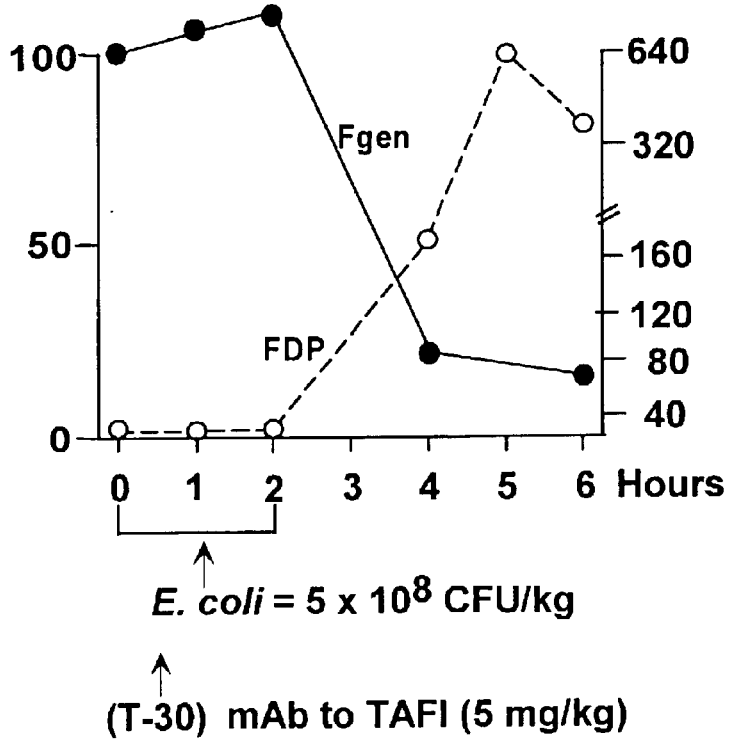

FIGS. 1A and 1B compare the fibrinolytic responses of baboons receiving sublethal dosages of *E. coli*, alone with those receiving sublethal *E. coli* plus anti TAFI mAb. The sublethal *E coli* group (N=6) and the experimental animal receiving both sublethal *E. coli* and the antibody to TAFI were permanent (i.e., greater than seven day) survivors. The fibrinolytic activity (FDP) and extent of fibrinogen consumption of the experimental animal was greater than that of the sublethal *E. coli* control group. The antibody titer after infusion of 5 mg/kg peaked at 4 to 6 micrograms/ml plasma and exhibited a half-life of approximately 6 hours. Experience in other studies has shown that coinfusion of non-immune mAbs of the same serotype as the TAFI mAb with *E. coli* does not exacerbate the host response.

These results indicate that TAFI also operates in this model of *E. coli* sepsis by influencing the fibrinolytic response.

TABLE 1

Antibody to TAFI Facilitates the Inflammatory Response to Sublethal *E. Coli* (SLEC)
SLEC + Anti-TAFI (Experimental) (N = 4) versus SLEC Alone (Control) (N = 3)

| | | Stage I | | | Stage II | | Stage III |
|---|---|---|---|---|---|---|---|
| Groups | T-30 | T-0 | +30 | +60 | +2 Hr | +4 Hr | +6 Hr | +24 Hr |
| | | | | TNF (ng/ml) | | | | |
| Experimental | 5 | 5 | 5 | 15.55 ± 3.56 | 20.34 ± 3.05 | 5 | 5 | 5 |

TABLE 1-continued

Antibody to TAFI Facilitates the Inflammatory Response to Sublethal *E. Coli* (SLEC)
SLEC + Anti-TAFI (Experimental) (N = 4) versus SLEC Alone (Control) (N = 3)

| Groups | Stage I | | | | Stage II | | | Stage III |
|---|---|---|---|---|---|---|---|---|
|  | T-30 | T-0 | +30 | +60 | +2 Hr | +4 Hr | +6 Hr | +24 Hr |
| Control | 5 | 5 | 5 | 5 | 7.26 ± 0.94 | 5 | 5 | 5 |
| Elastase/1 AT (nM) | | | | | | | | |
| Experimental | 4 | 4 | 5.1 ± 0.95 | 14.51 ± 7.67 | 25.75 ± 13.13 | 22.36 ± 10.01 | 28.27 ± 12.36 | 29.92 ± 3.81 |
| Control | 4 | 4 | 4 | 4 | 4.32 ± 0.23 | 7.02 ± 2.14 | 6.92 ± 2.06 | 5.12 ± 0.31 |
| WBC | | | | | | | | |
| Experimental | 9.5 ± 2.62 | 7.58 ± 1.68 | 4.73 ± 0.57 | 3.83 ± 0.76 | 0.98 ± 0.13 NA | 2.03 ± 0.43 | 2.18 ± 0.34 | 15.2 ± 3.54 |
| Control | 6.5 | 6.57 ± 0.07 | 8.8 | 5.3 ± 1.11 | 4.4 ± 2.02 | 6.07 ± 2.28 | 8.53 ± 3.44 | 18 ± 0.07 |
| IL-6 (ng/ml) | | | | | | | | |
| Experimental | 0.5 | 0.5 | 0.57 ± 0.06 | 4.21 ± 1.21 | 52.46 ± 2.87 | 102.19 ± 14.69 | 86.86 ± 34.94 | 3.36 ± 2.47 |
| Control | 0.34 | 0.69 ± 0.12 | 0.31 | 1.03 ± 0.13 | 10.82 ± 3.73 | 14.96 ± 3.68 | 14.09 ± 3.81 | 0.85 ± 0.14 |
| TAT (nM) | | | | | | | | |
| Experimental | 1 | 1.22 ± 0.19 | 1.13 ± 0.11 | 1.18 ± 0.1 | 2.24 ± 0.52 | 4.9 ± 1.55 | 6.32 ± 1.96 | 1 |
| Control | 1 | 1.27 ± 0.22 | 1 | 2.37 ± 1.12 | 1.47 ± 0.38 | 1.9 ± 0.6 | 1.66 ± 0.28 | 1 |
| FDP (μg/dl) | | | | | | | | |
| Experimental | 10 | 10 | 10 | 10 | 27.5 ± 15.16 | 127.5 ± 62.99 | 282.5 ± 116.85 | 360 ± 87.18 |
| Control | 10 | 10 | 10 | 10 | 10 | 33.33 ± 19.05 | 60 ± 40.82 | 15 ± 3.54 |

Table 1 extends studies on the role of endogenous TAFI in the sublethal *E. coli* model by comparing the inflammatory responses to sublethal *E. coli* alone with those following sublethal *E. coli* plus anti-TAFI antibody. This table lists the responses of some of the principle inflammatory and hemostatic factors of the baboon following infusion of sublethal *E. coli*. This sublethal model shows the three stages more distinctly, which otherwise would be compressed into a single stage with overlapping components. Most importantly, it shows that blockade of the endogenous TAFI protective response to sublethal *E. coli* profoundly increases the inflammatory response. Specifically, this table shows that the first stage (0–2 hrs) is dominated by TNF and neutrophil elastase both of which peak at T+2 hours, which in the case of the experimental group (sublethal *E. coli* plus anti TAFI antibody) are four to six fold higher than the control group (sublethal *E. coli* alone). These peaks coincide with the nadirs of the white blood cell counts, which in the case of the experimental group are four-fold lower than those of the control group. This indicates a more complete and sustained margination of neutrophils on to their microvascular endothelial target. In the second stage (2–6 hrs), the IL-6 and elastase concentrations remain elevated or continue to rise maintaining concentrations that in the experimental group are four to six fold higher than the control group. This is matched in the experimental group by a sustained depression of the white blood cell count while that of the control group rises to baseline and above. During all these second stage events, the TNF concentration of both groups returns toward baseline while the TAT concentration of the experimental group continues to rise into Stage IV. The coincidence of the depressed white blood cell counts, the sustained elevation of both elastase and IL-6 suggests an intense neutrophil/endothelial interaction with release of neutrophil proteases and endothelial injury. Into this volatile setting are fed increasing concentrations of chemotactically active (Gross, et al., Thromb Haemost, 77(5):894–900, 1997; Leavell, et al., Am. J. Respir. Cell Mol. Biol. 14:53–60, 1996) fibrin degradation products (FDP) beginning at the end of the first stage, which in the case of the experimental group rise to concentrations that are four to six fold higher than the control group. Finally, Stage III begins after a transition phase at T+8 to 12 hrs and extends to T+48 hrs. This exhibit shows that at T+24 hrs there is a "second round" of self-propagating inflammatory activity in which the elastase and FDP concentrations of the experimental group reach peak values, while those of the control group return toward baseline.

FIG. 2 shows the response to sublethal *E. coli* alone with that following sublethal *E. coli* plus anti-TAFI antibody. First, this figure shows that in the case of administration of sublethal *E. coli*, there is a surprising appearance of C5a in Stage III and in much larger amounts than in Stage I. Second, this figure shows that coinfusion of anti-C5a antibody with sublethal *E. coli* can increase the amount of C5a produced by two-fold. This data strongly suggest that C5a plays an important role in the inflammatory response to *E. coli*/endotoxin and that endogenous TAFI can play role in regulating this aspect of the inflammatory response. First, just like the baboon, the studies of the human responses to endotoxin show that complement activation occurs not only early on during Stages I and II, but also in even larger amounts at T+24 hrs during Stage III following reperfusion and the oxidative stress induction of MLP (Collard, et al. Am. J. Pathol. 156:1549–1556 (2000)). Second, the rat cecal ligation puncture model shows that both C5a was produced and C5a receptor was expressed during the sepsis response and that the rate of mortality was significantly reduced with antibodies to C5a and C5a receptor (Riedmemann, et al., J. Clin. Invest. 110(1):101–108 (2002); Laudes, et al., Am. J. Path. 160(5):1867–1875 (2002)). Third, Watanabe, et al, 2001 Thromb Res. 104:1–6, have shown that both TAFI antigen and activity were reduced in patients with disseminated intravascular coagulopathy (DIC) (5), and finally Campbell, et al, 2002 Microbiol Immunol, 46(2):131–134, demonstrated that TAFIa (procarboxypeptides R) inactivated C3a and C5a polypeptides (Campbell, et al., Microbiol. Immunol. 46(2):131–134 (2002)).

Role of TAFI ($LD^{100}$ E. coli Model)

Endogenous TAFI also influences the fibrinolytic and inflammatory response to $LD^{100}$ E. coli as shown in FIGS. 3 and 4.

Figures 3A, 3B:
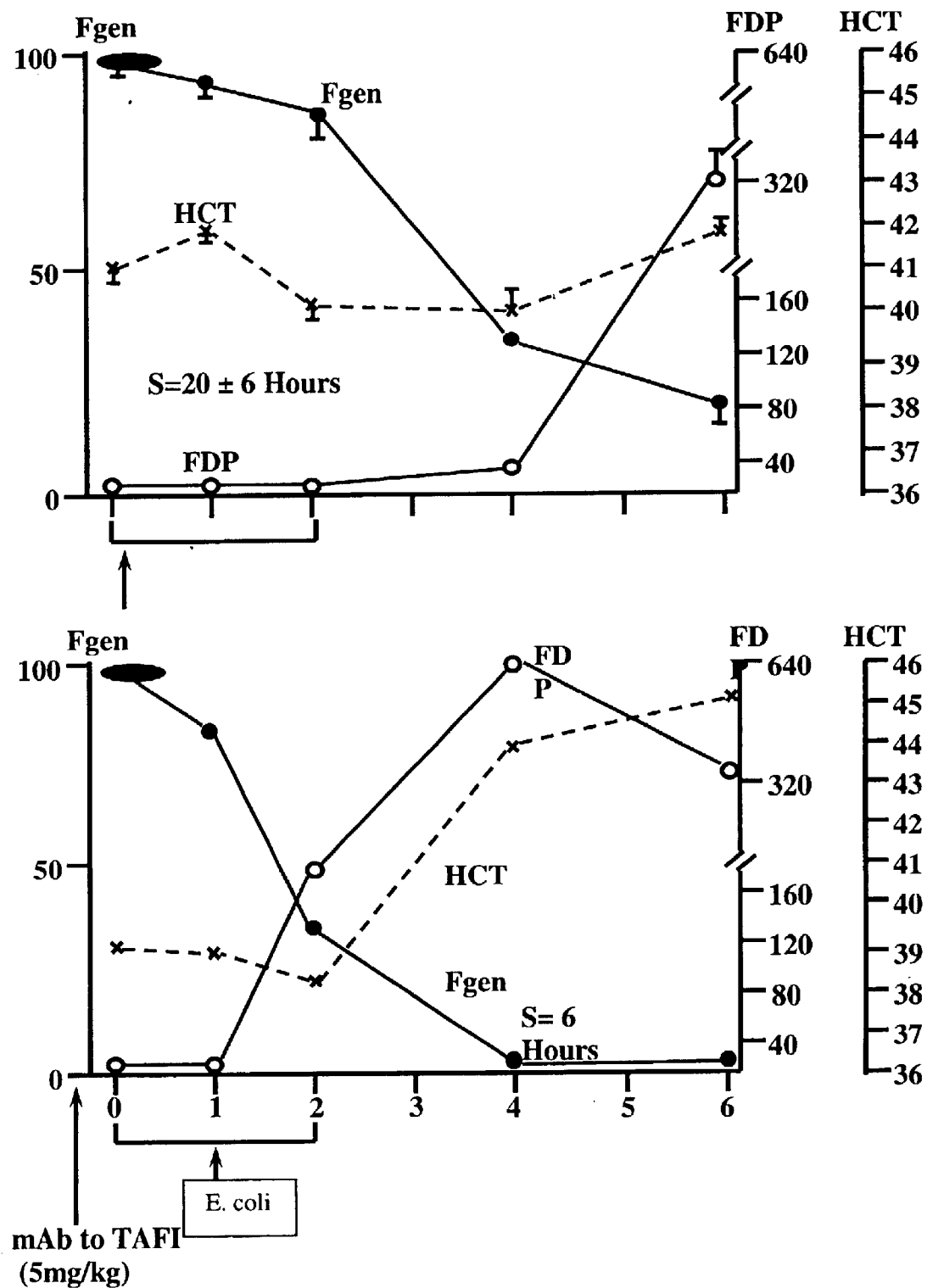
FIGS. 3A and 3B compare the fibrinolytic responses of baboons infused with $LD_{100}$ $E.$ $coli$ alone (FIG. 3A) with that of a baboon infused with $LD_{100}$ $E.$ $coli$ plus anti-TAFI mAb (FIG. 3B).

The baboons in FIGS. 3A and 3B both received $2-5\times10^{10}$ CFU/kg E. coli infused over a two-hour period. Treatment animal (FIG. 3B) also received 5 mg mAb to TAFI/kg body weight 30 minutes before initiation of the bacterial infusion. Samples were collected at T-0, 1, 2, 4, and 6 hours. FIGS. 3A and 3B compare the fibrinolytic responses of baboons receiving lethal dosages of E. coli, alone with those receiving lethal E. coli plus anti-TAFI mAb. The $LD_{100}$E. coli (N=6) group survived an average of 28 hours, while the experimental animal receiving both $LD_{100}$E. coli plus anti TAFI mAb died in six hours. The gross post mortem findings included 10 ml, 30 ml, and 50 ml of fluid in the pericardial, pleural, and peritoneal cavities of the experimental animal, whereas no more than one-tenth of these volumes was observed in the $LD_{100}$E. coli group. These findings were accompanied by histologic evidence of 3+ congestion of the spleen, liver, adrenal, and lungs, on a scale of 0 to 4, with only 1 to 2+ congestion of these organs in the $LD_{100}$E. coli group. In addition, the experimental animal exhibited a rise in hematocrit from 38 to 44 mm in six hours, whereas the hematocrit remained stable at 40 to 42 mm in the $LD_{100}$ E. coli group. Finally, the fibrinolytic activity (FDP) and the extent of fibrinogen consumption of the experimental animal were greater than that of the $LD_{100}$E. coli control group. The blood pressures of the control group and the experimental group both reached a nadir of 50 mm Hg just before death. The antibody titer after infusion of 5 mg/kg peaked at 4 to 6 micrograms/ml plasma and exhibited a half-life of approximately 6 hours. Experience in other studies has shown that coinfusion of non-immune mAbs of the same serotype as the TAFI mAb with E. coli does not exacerbate the host response.

These results indicate that TAFI operates in this model of E. coli sepsis by influencing the fibrinolytic response to E. coli. These observations also indicate that $LD_{100}$E. coli activation of vasoactive peptides can be attenuated by TAFI.

FIG. 4 shows the C5a response to $LD_{100}$E. coli. It is produced in larger amounts than that following sublethal E. coli (FIG. 2). It is produced in Stage I instead of Stage III, and it peaks at T+30 minutes, a full 60 minutes before TNF peaks and before the WBC, count reaches its nadir. This data confirms the observation of Ward, et al (Riedemann, et al., J. Clin. Invest. 110(1):101–108 (2002); Laudes, et al., Am. J. Path. 160(5):1867–1875 (2002)) and strongly suggests that C5a is an early and an important initiator of the inflammatory response and acts on sequence with TNF to drive the neutrophil endothelial interaction.

Methods of Treatment

Intravenous administration of the TAFI or TAFIa involves boluses in conjunction with a continuous infusion of a more dilute solution, the concentration of which can be adjusted to accommodate the fluid needs of the patient. The drug may also be administered using a slow intravenous drip over a period of hours to days, depending on the clinical response of the patient. The response of the subject will be the primary determinant and this may vary widely depending on the particular needs of the subject and the inflammatory event involved. However, it will be noted that in general, rescue or therapeutic doses will be higher than doses required in prophylactic treatment. It is anticipated that species differences between baboons and humans will require adjustment of the total amount of and rate of TAFI administration (dose finding) in humans when extrapolating from the data in the accompanying figures, since the TAFI in these studies was baboon TAFI used in baboons. This includes increasing duration of infusion to depending on status and response of patient.

If signs of an inflammatory response occur, the infusion rate should be increased and perhaps a bolus given. If the clinical signs indicate stabilization of the subject's condition, the infusion rate may be gradually decreased. When the signs continue to be stable as the dosage is decreased, the infusion may be discontinued.

An effective amount of the TAFI or TAFIa is administered to a subject in need of such treatment. In the case of activated protein C, this was recently demonstrated in clinical trials to be an amount effective to rescue approximately 20 percent of the patients treated. The composition preferably is administered intravenously, and preferably a combination of a dilute continuous infusion with boluses as needed, as described previously. In treating a subject to inhibit or to reverse the dysfunctional responses, the subject's clinical signs are measured regularly and the dosage of activated protein C (if also administered) and TAFI adjusted accordingly.

A preferred on-line method for monitoring the coagulopathic dysfunction is frequent measurement of the subject's fibrin degradation product and fibrinogen levels. Fibrin degradation products may be measured on-line using a standard visual precipitation assay. Fibrinogen levels also may be measured by thrombin clotting time expressed in percent of control, the normal level being 100% of control (See Tables 2 and 3). Measurement of changes of vital signs and in white cell count over time may also be required as a surrogate on-line marker of neutrophil inflammatory activity (See Tables 2 and 3). In those situations where a dysfunctional inflammatory response has not yet become clinically apparent but is expected to occur, such as in the first several hours of a serious crush or burn injury, continuous intravenous therapy may be initiated before the clinical signs indicate onset of coagulopathy or permeability dysfunction. The subject should be monitored closely. If the fibrin degradation product level rises above 20 to 40 µg/dl, indicating onset of coagulation dysfunction, or the vital signs and blood pressure indicate onset of permeability dysfunction, the dosage should be increased and perhaps a bolus given, to quickly raise the plasma level of the protein. When the subject's clinical condition appears to stabilize, the administration rate may be gradually decreased, and finally discontinued, as described above.

When the subject is in shock or other signs or symptoms, such as a falling fibrinogen level, indicate that a dysfunctional response already is in progress, the treatment method would be the same except that the initial administration rate should be higher.

It will of course be understood that clinically, human patients usually present in a wide variety of conditions and with different stimuli. Sepsis may result from exposure to either gram negative or gram positive bacteria. Other variables may play a role, including other disease conditions and reactions (both favorable and unfavorable) to other drugs or treatments. The baboon model is typically viewed as an extreme-intravenous injection of a lethal dosage of E. coli. Moreover, it has a defined beginning, and is usually undertaken with normal animals. Clinically, sepsis is usually a sequella to another event, such as pneumonia, childbirth, or cancer.

The method described herein is directed to the treatment of dysfunctional endothelial cells wherein the endothelium is characterized by loss of selective permeability or wherein the subject experiences coagulation abnormalities of the type described, or both. Treatment can be prophylactic, to prevent the dysfunctional inflammatory response in high-risk subjects, or in those clinical settings where such dysfunction is imminent or likely. Treatment can be therapeutic to rescue subjects from a dysfunctional response already in progress.

The prophylatic (early intervention) use of TAFIa during Stages I and II is based on the rate of appearance of C5a as shown in FIGS. 2 and 4. C5a peaks at T+30 minutes followed by, 1) the margination of white blood cells as reflected by the fall in the white blood cell count, which reaches its nadir at T+60 to 120 minutes and by, 2) elastase activity which peaks at T+60 to 120 minutes. A sufficient amount of TAFIa must be delivered to attenuate but not completely block the C5a and margination of the white blood cells (neutrophils). In this prophylatic model APC also is delivered attenuating the production of both TNF and chemotactically active fibrin degradation products (FDP).

The therapeutic (intervention at T+2–6 hours) use of TAFIa during Stages II and III is based on the observation that if the subject survives Stages I & II and goes on to Stage III there is a "second round" of inflammatory activity and including a delayed or second peak of C5a activity as shown in FIG. 2. This coincides with a sustained depression of the white blood cell count and the sustained appearance of elastase activity in those subjects that go on to die later. FIG. 2 shows the sublethal model in which a weak early generation of C5a is followed by a stronger peak of activity at T+24–48 hours. This figure also shows that addition of anti TAFI antibody increases the peak activity of C5a. This observation coincides with the increased sustained inflammatory activity documented during Stage III shown in Table 1, and it coincides with the enhancing effect of anti TAFI antibody on this inflammatory activity, which also is shown in Table 1. The sustained depression of the white cell count is assumed to be a product, at least in part, of the sustained recruitment and attack on the target microvascular endothelium driven by C5a as well as possible bone marrow depression. Since TNF has returned to baseline, the therapeutic use of TAFI in this case is to limit this sustained recruitment by raising the white cell count with TAFIa while continuing to reduce the generation of chemotactically active fibrin degradation products with activated protein C.

TABLE 2

Method of Prophylatic Treatment of *E. coli* Sepsis with TAFI and APC

| | Stage I–II (0–6 Hrs) |
|---|---|
| T-0 | Begin TAFI infusion at 4–8 μg/kg/min. and continue out to 360 minutes. If necessary, give additional bolus infusions of 1 to 2 mg each of TAFI every 20 minutes out to 120 minutes to limit the fall in WBC count to within 10% baseline during each 20-minute interval (or to approximately 2,000/mm$^2$ at T + 120). WBC counts are to be run every 20–30 minutes. |
| T + 30 minutes | Begin APC infusion at 8–16 μg/kg/min. Continue out to 360 minutes minutes and adjust to keep FDP between 40 and 160 μg/dl. If necessary, give additional bolus infusion of 5 to 10 mg each every 20–30 minutes beginning at T + 120 minutes and continue out to 360 minutes. FDP levels to be run every 20 to 30 minutes. NOTE: The coadministration of TAFI should reduce the amount of APC needed by one-half or more. Total APC for a 10 kg animal is reduced from 20 mg to 10 mg or less over the first 360 minutes. |
| | Stage III (6–48 Hrs) |
| [Transition] | 360 to 420 minutes |
| T + 420 to 720 minutes | Continue minimum infusion rates of 4 μg/kg/min and 8 μg/kg/min of TAFI and APC respectively to maintain WBC at approximately 2,000 and FDP to ≦160 μg/dl out to 72 minutes. If necessary, use bolus infusions as described above. Total APC for a 10 kg animal is reduced from 40 to 20 mg or less over the full 720 minutes of the study. |

TABLE 3

Method of Therapeutic Treatment of *E. coli* Sepsis with TAFI and APC
Stage II and III (2–12 Hrs)

| T + 120 Minutes | Begin TAFI infusion at 8 to 16 mg/kg/min and continue out to 360 minutes. If necessary administer bolus infusions of 2 to 4 mg each every 20–30 minutes out to 180 to 240 minutes to raise the WBC count 1½ to 2 fold above is nadir (e.g., 1,000/mm$^3$ to 2,000/mm$^3$). Begin APC infusion at 16 to 32 μg/kg/min and continue out to 360 minutes and adjust to keep FDP between 40 to 160 μg/kg/dl. If necessary administer bolus infusion of 10 to 15 mg each every 20–30 minutes and continue out to 360 minutes. NOTE: This should reduce the amount of APC needed by one-half or more and increase the survival rate from 20–30% to 50% or more. Total APC for 10 kg animal is reduced from 100 mg to 50 mg over the first 360 minutes. |
|---|---|
| T + 360 to 420 minutes | Transition Period |
| T + 420 to 720 minutes | Continue minimum infusion rates of 4 μg/kg/min and 8 μg/kg/min of TAFI and APC respectively to maintain WBC at 2,000 and FDP to ≦160 μg/dl out to 720 minutes. If necessary, use bolus infusions as described above. Total APC for a 10 kg animal is reduced from 200 to 100 mg or less over the full 720 minutes of the study. |

We claim:

1. A method for treating or preventing symptoms of a disorder associated with dysfunctional endothelium comprising administering to a patient in need thereof active ingredients consisting essentially of an effective amount of thrombin-activatable fibrinolysis inhibitor (TAFI) in combination with activated protein C (APC) to alleviate symptoms of the disorder associated with increased permeability of the endothelium and a rise in fibrin degradation products.

2. The method of claim 1 wherein the disorder is sepsis.

3. The method of claim 1 wherein the disorder is disseminated intravascular coagulation.

4. The method of claim 1 wherein the patient is a human.

5. The method of claim 1 wherein the amount of TAFI is effective to restore normal fibrinolysis.

6. The method of claim 1 wherein the patient is treated prophylactically.

7. The method of claim 1 wherein the patient is treated therapeutically.

8. The method of claim 1 wherein TAFI is infused at 4–8 µg/kg/min.

9. The method of claim 8 wherein the TAFI is infused over a period of at least 360 minutes.

10. The method of claim 8 wherein additional bolus infusions of 1 to 2 mg each of TAFI are administered to the patient.

11. The method of claim 8 comprising infusing APC at 8–16 µg/kg/min.

12. The method of claim 11 further comprising administering bolus infusions of 5 to 10 mg each of APC.

13. The method of claim 1 wherein TAFI is infused at 8 to 16 mg/kg/min.

14. The method of claim 13 further comprising administering bolus infusions of 2 to 4 mg each of TAFI.

15. The method of claim 14 further comprising infusing APC at 16 to 32 µg/kg/min.

16. The method of claim 15 further comprising administering bolus infusions of 10 to 15 mg.

* * * * *